United States Patent [19]
Romare

[11] Patent Number: 6,027,484
[45] Date of Patent: *Feb. 22, 2000

[54] PANT DIAPER OR SANITARY PANTY HAVING A DETACHABLY CONNECTED FRONT PART

[75] Inventor: Anette Romare, Mölndal, Sweden

[73] Assignee: SCA Hygiene Products AB, Goteborg, Sweden

[ * ] Notice: This patent issued on a continued prosecution application filed under 37 CFR 1.53(d), and is subject to the twenty year patent term provisions of 35 U.S.C. 154(a)(2).

[21] Appl. No.: 08/714,111
[22] PCT Filed: Apr. 11, 1995
[86] PCT No.: PCT/SE95/00389
    § 371 Date: Sep. 30, 1996
    § 102(e) Date: Sep. 30, 1996
[87] PCT Pub. No.: WO95/27460
    PCT Pub. Date: Oct. 19, 1995

[30] Foreign Application Priority Data

Apr. 12, 1994 [SE] Sweden .................................. 9401224

[51] Int. Cl.⁷ ...................................................... A61F 13/15
[52] U.S. Cl. .......................... 604/386; 604/391; 604/393; 604/394
[58] Field of Search .............................. 604/385.1, 385.2, 604/389, 390, 391, 393, 394, 396, 386

[56] References Cited

U.S. PATENT DOCUMENTS

| | | | |
|---|---|---|---|
| H1674 | 8/1997 | Ames et al. | 604/396 |
| 4,936,840 | 6/1990 | Proxmire | 604/391 |
| 5,069,678 | 12/1991 | Yamamoto et al. | 604/358 |
| 5,074,854 | 12/1991 | Davis | 604/396 |
| 5,106,385 | 4/1992 | Allen et al. . | |
| 5,163,932 | 11/1992 | Nomura et al. | 604/396 |
| 5,261,901 | 11/1993 | Guay | 607/391 |
| 5,269,776 | 12/1993 | Lancaster | 604/391 |
| 5,366,453 | 11/1994 | Zehner et al. | 604/391 |
| 5,368,585 | 11/1994 | Dokken | 604/391 |
| 5,370,634 | 12/1994 | Ando et al. | 604/393 |
| 5,531,732 | 7/1996 | Wood | 604/391 |
| 5,624,420 | 4/1997 | Bridges et al. | 604/396 |
| 5,624,428 | 4/1997 | Sauer | 604/391 |

FOREIGN PATENT DOCUMENTS

| | | |
|---|---|---|
| 0 323 634 A2 | 7/1989 | European Pat. Off. . |
| 0 532 034 A2 | 3/1993 | European Pat. Off. . |
| 27 31 911 | 2/1979 | Germany . |
| 2 267 024 | 11/1993 | United Kingdom . |

*Primary Examiner*—Mark O. Polutta
*Attorney, Agent, or Firm*—Burns, Doane, Swecker & Mathis, L.L.P.

[57] ABSTRACT

A pant diaper or a sanitary panty which includes a front part, a rear part, and an intermediate crotch part, which includes an absorbent body enclosed between an inner and an outer casing sheet. The front part is detachably joined to the rear part by means of a first fastening. A piece of flexible material extends over the front part and is joined thereto over a larger part of its surface by means of a first releasable fastening, which extends on both sides of a centrally located region of the piece of material, from the edges of the central region to the respective side edges of the front part. The piece of material is also joined to the rear part.

13 Claims, 2 Drawing Sheets

PANT DIAPER OR SANITARY PANTY HAVING A DETACHABLY CONNECTED FRONT PART

TECHNICAL FIELD

The present invention relates to a pant diaper or a sanitary panty which includes a front part, a rear part and an intermediate crotch part and an absorbent body enclosed between an inner and an outer casing sheet, wherein the front part is detachably joined to the rear part by means of a first fastening.

BACKGROUND OF THE INVENTION

So-called all-in-one diapers are being replaced to an ever greater extent with pant diapers, sometimes called training pants, for slightly older diaper-wearing children. Pant diapers have a number of good features. They fit well on the wearer, are easy to put on and take off with the child in a standing position, sit firmly in place after having been put on to a child, and conform to the anatomy of the child as the child moves, in a comfortable fashion. Pant diapers also resemble conventional underpants and it is easy to understand how the pant diaper shall be used, thereby in many instances enabling somewhat older diaper-wearing children to perform themselves the simple operations required when putting on the pant diaper. Pant diapers, however, also have certain drawbacks. They are difficult to change with the user lying on his/her back and when changing the pant diaper it is necessary to remove completely any article of clothing that is worn on top of the diaper. Neither can a used pant diaper be rolled-up and sealed in a bag in the same way that an all-in-one diaper can. In addition, a soiled pant diaper that contains feces is liable to soil the wearer when removing the pant diaper.

GB-A-2 267 024 teaches a pant diaper of the aforesaid kind which is intended to eliminate these drawbacks. The first releasable fastening is comprised of weakening lines in the front part, close to respective side edges thereof, and the refastenable fastening is comprised of fasteners of the hook and loop type attached to flaps which extend from respective side-edge connections between the front and rear part, slightly inwards over the front part. Many hand maneuvers are required to open such a pant diaper, while opening of the pant diaper is made difficult by the fact that the weakening lines are relatively inaccessible. Moreover, the join formed by the weakening lines complicates manufacture of the pant diaper.

SUMMARY OF THE INVENTION

An object of the present invention is to provide a pant diaper which, similar to the aforesaid known pant diaper, eliminates the drawbacks of conventional pant diapers, and which can be opened easily with a few hand movements and which can be readily manufactured.

This object is achieved in accordance with the invention with a pant diaper or sanitary panty of the kind defined in the introduction which is characterized in that a piece of flexible material extends over said front part and is joined thereto over a large part of its surface by a first releasable fastening which extends on both sides of a centrally located region of the piece of material, from the side edges of the central region to respective side edges of the front part, and in that said piece of material is also joined to the rear part. Because the first fastening extends over a large surface, it is possible to dimension this fastening with a high degree of safety so that the forces that are generated when the pant diaper is in use, particularly when putting-on the pant diaper, will be taken-up by the first fastening with a good margin, while, at the same time, enabling the fastening to be readily released by successively removing the piece of flexible material from said front part.

In one preferred embodiment of the invention said piece of material is connected refastenably with the front part by means of a second fastening and the first fastening means is destroyed when releasing the fastening. The first fastening may conveniently consist of a sparsely configured weld or glue pattern, and the piece of material is elastic and mounted in a stretched state, so as to function as waist elastic. Provided in the centre region of said piece of material is a means for dividing said piece into two parts which extend from the central region to respective side edges of the pant diaper, and a second refastenable fastening is provided between the piece of material and said front part, on both sides of a longitudinal symmetry line of the pant diaper, within said central region, said fastening joining each of the two parts of the piece of material to the front pant diaper part.

BRIEF DESCRIPTION OF THE DRAWINGS

The invention will now be described with reference to the accompanying drawings, in which.

DETAILED DESCRIPTION OF THE PREFERRED EMBODIMENT

Figure 1:
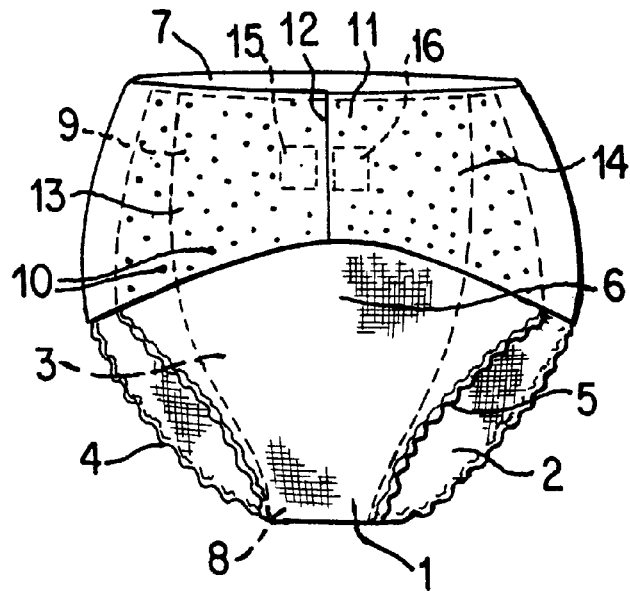
FIG. 1 is a schematic front view of one embodiment of an inventive pant diaper.
Figure 2:
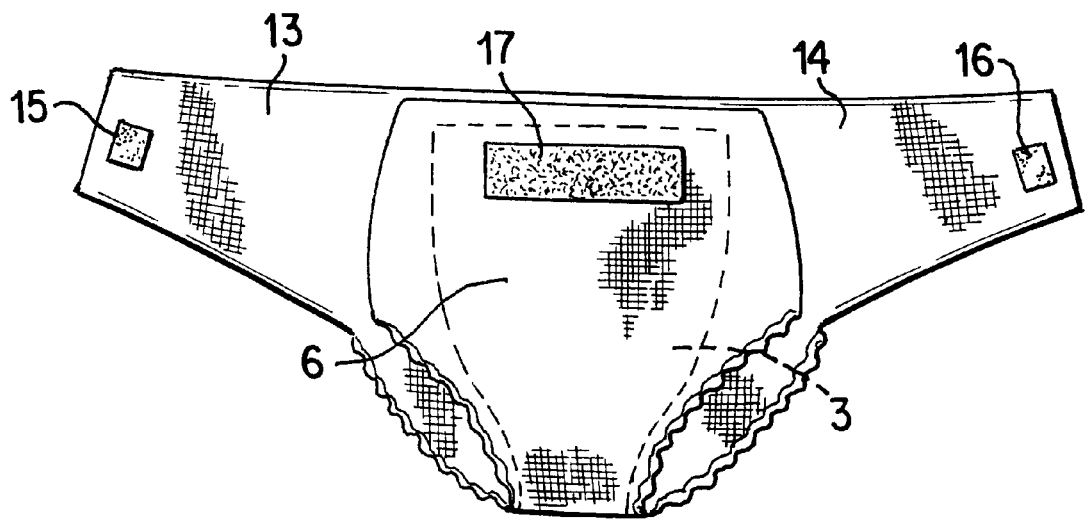
FIG. 2 is a front view of the pant diaper of FIG. 1 and shows the diaper in an opened-out state.

FIGS. 1 and 2 illustrate a pant diaper according to a first embodiment of the invention. A pant diaper is intended to be put on in the same way as a pair of underpants, and is characterized by an elastic waist part which can be stretched so as to enable the pant diaper to be easily pulled over the wearer's hips when putting on and taking-off the pant diaper, and which has an elasticity such as to ensure that when worn the pant diaper will be held securely in place by the contraction forces exerted by the elastication in the waist part of the pant diaper. In order to fulfill these functional requirements while, at the same time, limiting the number of product sizes, the pant diaper will preferably have a stretchability which is greater than 80%, i.e. it shall be possible to stretch the waist part to an extent which corresponds to 1.8 times the circumference of the waist part of a pant diaper in a relaxed or non-stretched state. When the diaper is worn, the combined contraction force in the waist part, i.e. the sum of the forces exerted by the elastic provided in the front part, the rear part and the side parts will preferably exceed 3 N.

The pant diaper illustrated in FIG. 1 and 2 is suitably constructed in the same way as the pant diaper described in Swedish Patent Application No. 9200663-4, that is, it will include an absorbent body 1 enclosed between an inner and an outer casing sheet 2 and 3 respectively. The inner casing sheet 2 is liquid-permeable and is comprised, for instance, of nonwoven material compiled from fibres of polyethylene, polypropylene, polyester or mixtures thereof. Viscose fibres may also be used. It is also conceivable to form the inner casing sheet from a perforated plastic sheet, for instance a perforated polyethylene sheet. The outer casing sheet 3 is liquid-impermeable or at least hydrophobic and may, for instance, comprise a sheet of polyethylene or nonwoven material which has been coated with or laminated with polyolefins so as to become liquid-impermeable or at least hydrophobic. For aesthetic and psychological reasons, the outer casing sheet 3 may be comprised of two layers, an inner, liquid impermeable layer and a layer of textile-like material placed outside the inner layer. The wearer will then see and feel the pant diaper as being less of a plastic garment. When the outer casing sheet has this latter construction, it is not necessary for the liquid-impermeable sheet to have the same extension as the textile or fabric-like sheet, but may be smaller than said sheet, for instance liquid-impermeable casing material can be omitted from the side parts of the pant diaper.

The absorbent body 1 may, for instance, contain cellulose fluff pulp with or without an admixture of particles of so-called superabsorbent material and/or thermoplastic melt fibres, and may be comprised of one or more layers.

Similar to a pair of underpants, the pant diaper illustrated in FIG. 1 and 2 has a waist opening and two leg openings, which are provided conventionally with leg elastic 4, 5. The pant diaper is put on by inserting the legs of the wearer through the leg openings and then drawing the pant diaper up over the wearer's hips. The contraction forces exerted by the elastic elements in the waist opening, i.e. in the uppermost part of the waist part, are preferably greater than the contraction forces exerted in the remainder of the waist part. This will ensure that the pant diaper remains seated in its intended position, even when the absorbent body is saturated with absorbed urine.

The pant diaper includes a front part 6, a rear part 7 and an intermediate crotch part 8. A piece of material 9, which is made of fibrous nonwoven material or of plastic material and which is elastic or has been made elastic in some suitable manner, extends transversely across the front part 6 between its side edges, and is joined to the rear part at those portions thereof which lie laterally outside the front part of the pant diaper. The piece 9 is joined to the outer casing sheet 3 of the front part of the pant diaper by a sparsely configured pattern of welding or gluing points 10, this pattern extending over essentially the whole of said piece of material with the exception of a region 11 which is central in relation to the longitudinal symmetry line of the pant diaper. The piece of material 9 is divided into two parts 13, 14, by a separation line 12 which extends along the longitudinal symmetry line of the pant diaper. Refastenable fastener means are mounted within the central region 11 on both sides of the separation line 12. These refastenable fastener means may, for instance, have the form of hook and loop means, for instance of the Velcro-type with the outwardly projecting hook means containing male parts 15, 16 provided on the piece of material 9. In the illustrated embodiment, the looped female parts 17 of the fastener devices are integrated to form a band or strip mounted on the casing sheet 3.

As will be seen from FIGS. 1 and 2, the aforesaid two parts 13, 14 form flaps which project out from the casing sheet of the rear part of the pant diaper and are thus integral with aid rear part. It will be understood, however, that the two arts 13, 14 may instead be comprised of pieces that are separate from the rear part of the pant diaper and which have been attached to the side edges thereof in some suitable manner, for instance welded thereto.

The described pant diaper can be removed and changed without needing to remove trousers or a like garment worn on top of the pant diaper, simply by gripping the loose flaps formed by the separating line 12 in the central region 11, and pulling the two parts 13, 14 of the piece 9 loose from the front part 6. This is easily done, since only a few of the fastening points 10 between the outer casing sheet 3 and the piece of material 9 need be broken simultaneously when pulling the parts 13, 14 from the front part of the pant diaper. When the parts 13, 14 have been loosened completely from the front part, the pant diaper will have the configuration shown in FIG. 2 in which the front part is no longer connected to the rear part. The rear part or the front part of the pant diaper can then be inserted between the legs of the wearer. A replacement pant diaper can then be placed on the wearer, by loosening the front part of the pant diaper in the aforedescribed manner and then inserting the front or the rear part of the replacement diaper between the wearer's legs. The side parts are then fastened together, by refastening the pant diaper with the aid of the fastener means 15–17, whereafter the pant diaper can be pulled up to its correct final position in the same way as a pair of underpants, unless, of course, this has already been done in conjunction with refastening the pant diaper.

The removed pant diaper is rolled-up with the parts 13, 14 positioned as shown in FIG. 2, and the thus rolled-up pant diaper is secured in package form, by tying together the pants diaper parts 13, 14 or by means of the fasteners 15–17.

Figure 3:
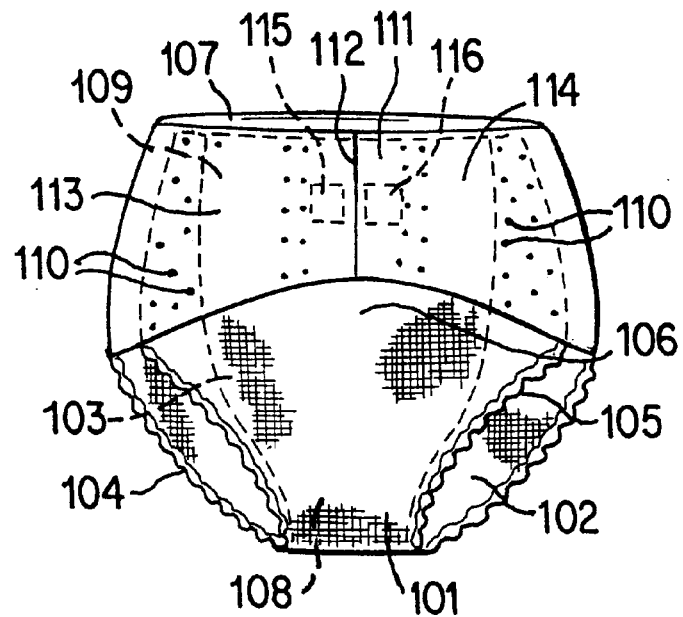
FIG. 3 is a view similar to FIG. 1 of a second embodiment of an inventive pant diaper.

The aforedescribed pant diaper can thus be opened by means of the readily accessible flaps, with just a few hand movements and in a simple and easily understood manner. It is also easy to dimension the fastening pattern so that the piece of material will remain securely fastened to the front part of the pant diaper in the case of all conceivable loads that can occur when using and handling the pant diaper, and at the same time to ensure that the number of fastening points that need to be broken simultaneously in order to release the piece of material from the outer casing sheet are so few in number as to enable the piece of material to be loosened by a suitable small force. The fastening pattern need not be homogenous, but may conveniently be more dense or have a greater strength at the side-edge portions of the front part of the pant diaper and the upper corner portions of said parts, so as to prevent these portions being folded-in against the wearer's body when putting-on the pant diaper. In FIG. 3 a second embodiment of a pant diaper according to the invention having such a non-homogenous fastening pattern is illustrated. The pant diaper of FIG. 3 differs from the diaper of FIG. 1 only in that it is provided with a different fastening pattern. Elements in the pant diaper shown in FIG. 3 similar to corresponding elements in FIG. 1 are therefore given the same reference numerals as in FIG. 1 with the addition of one hundred, and need not be further described. In the embodiment illustrated in FIG. 3 the non-homogenous pattern of fastening points 110 is interrupted on both sides of the central region 111 so that no fastening points are present in an area located between the central region and the respective side-edge portion. In order to permit such an interrupted pattern of fastening points and still enabling the loosening of the piece of material 109 by a suitable small force the sum of the areas containing fastening points must be sufficiently large. The material piece 109 of the embodiment disclosed in FIG. 3 should therefore have a sparsely configured pattern of fastening points 110 on at least 50% of its area, and preferably 75% of its area.

An inventive pant diaper is also easy to manufacture, since the manufacturing processes applied may be those applied conventionally with the addition of an extra welding or gluing operation. A used pant diaper can also be handled in a manner which is satisfactory from the aspect of hygiene.

In one variant of the described embodiments, an open pant diaper is refastened by tying together the separate parts 13, 14 and 113, 114 of the respective material piece 9, 109. This variant requires no refastenable fasteners of the Velcro-type or any other type.

In the described embodiments, the pieces of material 9, 109 form the waist elastic and are therefore mounted in a stretched state, wherein the rear part of the pant diaper may be provided with conventional waist elastic or may be free of such elastic. In another variant of the illustrated pant diapers, the pieces of material 9, 109 may also extend transversely across and be fastened to the rear part of the pant diaper, to form an all-round waist elastic.

In another embodiment of the invention (not shown) the means joining the piece of material and the front part of the pant diaper is refastenable adhesive coating. In this case the fastening is also comprised of a sparsely configured pattern of discrete gluing points. This fastening may conceivably have the form of mechanical refastenable fasteners, for instance of the hook and loop type, such as Velcro-fasteners. In this case, it is not necessary to provide refastenable fastener means in the central region. Of course, it is possible to include in the pattern of refastenable fastening points fastening points that are destroyed when opening the pant diaper for the first time.

It will be apparent from the aforedescribed embodiments that the fastening pattern shall extend over a large part of the surface of said material piece so that the load will be spread over a wide area, therewith enabling the fastenings to be formed in a manner which will enable them to be easily opened without risk of being broken when the pant diaper is in normal use.

Although the aforedescribed embodiments relate solely to pant diapers it will be understood that the invention can also be employed in the case of sanitary panties, i.e. underpants which have formed integrally therewith absorbent bodies which are intended to absorb menstrual fluid or light incontinence fluids.

Figure 4:
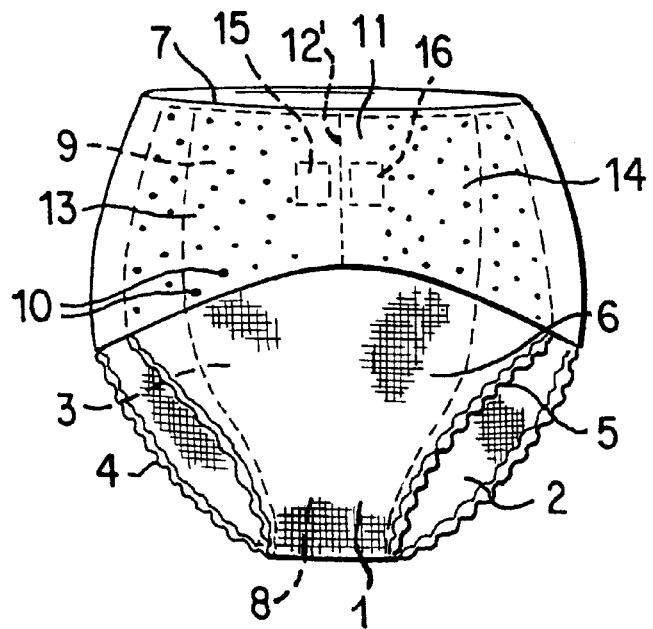
FIG. 4 is a schematic front view of a further embodiment of the inventive pant diaper.

It will also be understood that the described and illustrated embodiments can be modified within the scope of the invention. For instance, the separation line which divides the piece of material into two separate parts can be replaced by a line of perforations or a tear strip 12' as shown in FIG 4. The edges of the separation line can also be held together by releasable tape or the like. Neither need the piece of material be elastic, since the pant diaper may be provided with conventional waist elastic, e.g. elastic threads which have been mounted in a stretched state between the two casing sheets. Refastenable fastener means of types other than hook and loop types may be used, for instance refastenable adhesive fasteners, shape-bound fasteners that comprise beads and coacting grooves, and so on. The invention is therefore restricted solely by the contents of the following claims.

I claim:

1. A pant diaper or a sanitary panty comprising:

a front part having opposing side edges, a rear part, an intermediate crotch part, and an absorbent body enclosed between an inner and an outer casing sheet, wherein the front part is detachably joined to the rear part by a first fastening means to form a pant diaper including a circumferential waist opening and predefined leg openings prior to placement on a wearer;

wherein said first fastening means includes a piece of flexible material extending transversely over the front part between the side edges thereof, and having at least 50% of its surface joined to the front part by means of a first releasable fastening, the first releasable fastening extending on both sides of a centrally located region of said piece of material from the side edges of said central region to respective said side edges of said front part;

wherein the first releasable fastening is destroyed when loosening said first fastening means; and wherein the piece of material is also joined to the rear part.

2. The pant diaper or sanitary panty according to claim 1, further comprising a second fastening means, the piece of material being refastenably fastened to the front part by the second fastening means.

3. The pant diaper or sanitary panty according to claim 2, wherein the first releasable fastening is not refastenable.

4. The pant diaper or sanitary panty according to claim 1, wherein the first releasable fastening is comprised of a sparsely configured fastening pattern of weld or glue points.

5. The pant diaper or sanitary panty according to claim 4, wherein the fastening pattern is interrupted on both sides of the central region so that the piece of material is unattached to the front part in areas located between the respective side-edge part of the front part and the central region.

6. The pant diaper or sanitary panty according to claim 4, wherein the fastening pattern is denser in the side-edge parts of the front part and the upper corner parts of said front part than elsewhere.

7. The pant diaper or sanitary panty according to claim 1, wherein the piece of material is elastic the material being mounted over the front part in a stretched state and functions as waist elastic.

8. The pant diaper or sanitary panty according to claim 1, wherein the piece of material includes means in said central region for separating said piece of material into two parts, each said part extending from the central region to a respective side edge of the pant diaper or sanitary panty.

9. The pant diaper or sanitary panty according to claim 8, wherein the second refastenable fastening between the piece of material and the front part is located on both sides of a longitudinal symmetry line of the diaper or panty within said central region, wherein said fastenings fasten the two parts of the piece of material to the front part of the pant diaper or sanitary panty.

10. The pant diaper or sanitary panty according to claim 1, wherein the centrally located region of said piece of material is longitudinally disposed and the first releasably fastening extends on both sides of the longitudinal region.

11. The pant diaper or sanitary panty according to claim 1, wherein the first releasable fastening is disposed between an outer surface of the front part and an inner surface of the pie of material.

12. The pant diaper or sanitary panty according to claim 1, wherein said front part includes a waist portion generally adjacent said circumferential waist opening and a front portion extending between said circumferential waist opening and said predefined leg openings, said first fastening means extending generally over said waist portion and a substantial portion of said front portion.

13. A pant diaper or a sanitary panty comprising:

a front part having opposing side edges, a rear part, an intermediate crotch part, and an absorbent body enclosed between an inner and an outer casing sheet, wherein the front part is detachably joined to the rear part by a first fastening means to form a pant diaper including a circumferential waist opening and predefined leg openings prior to placement on a wearer, said first fastening means including a piece of flexible material extending transversely over the front part between the side edges thereof, and having at least 50% of its surface joined to the front part by means of a first releasable fastening, the first releasable fastening extending on both sides of a centrally located region of said piece of material from the side edges of said central region to respective side edges of said front part;

wherein the piece of material is also joined to the rear part; and wherein a second fastening means refastenably fastens the piece of material to the front part.

* * * * *